US012642499B2

(12) United States Patent
Hamauzu

(10) Patent No.: US 12,642,499 B2
(45) Date of Patent: Jun. 2, 2026

(54) IMAGING CONTROL DEVICE, IMAGING CONTROL METHOD, AND IMAGING CONTROL PROGRAM

(71) Applicant: FUJIFILM CORPORATION, Tokyo (JP)

(72) Inventor: Shin Hamauzu, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 164 days.

(21) Appl. No.: 18/817,183

(22) Filed: Aug. 27, 2024

(65) Prior Publication Data

US 2025/0090123 A1 Mar. 20, 2025

(30) Foreign Application Priority Data

Sep. 14, 2023 (JP) ................................. 2023-149249

(51) Int. Cl.
*A61B 6/00* (2024.01)
*A61B 6/40* (2024.01)
*A61B 6/42* (2024.01)
*A61B 6/58* (2024.01)

(52) U.S. Cl.
CPC .............. *A61B 6/54* (2013.01); *A61B 6/4014* (2013.01); *A61B 6/4266* (2013.01); *A61B 6/487* (2013.01); *A61B 6/566* (2013.01); *A61B 6/582* (2013.01)

(58) Field of Classification Search
CPC ..... A61B 6/4014; A61B 6/4266; A61B 6/487; A61B 6/54; A61B 6/566; A61B 6/582
See application file for complete search history.

(56) References Cited

U.S. PATENT DOCUMENTS

| | | | |
|---|---|---|---|
| 2015/0379711 A1 | 12/2015 | Imai | |
| 2016/0140720 A1 | 5/2016 | Naito | |
| 2017/0221207 A1 | 8/2017 | Imai | |
| 2018/0122094 A1 | 5/2018 | Naito | |
| 2019/0175941 A1* | 6/2019 | Miyazaki | ............. A61B 6/5217 |

FOREIGN PATENT DOCUMENTS

| | | |
|---|---|---|
| JP | 2014-207958 A | 11/2014 |
| JP | 2015-043959 A | 3/2015 |
| JP | 2019-087892 A | 6/2019 |

* cited by examiner

*Primary Examiner* — Mark R Gaworecki
(74) *Attorney, Agent, or Firm* — SOLARIS Intellectual Property Group, PLLC

(57) ABSTRACT

A processor mutually registers another fluoroscopy apparatus other than a fluoroscopy apparatus of which the imaging control device itself controls the fluoroscopy, and notifies, in a case in which an instruction to start emitting radiation is given and the radiation is emitted from the fluoroscopy apparatus of which the imaging control device itself controls the fluoroscopy, the other fluoroscopy apparatus that the radiation has been emitted.

13 Claims, 10 Drawing Sheets

IMAGING CONTROL DEVICE, IMAGING CONTROL METHOD, AND IMAGING CONTROL PROGRAM

CROSS REFERENCE TO RELATED APPLICATIONS

The present application claims priority from Japanese Patent Application No. 2023-149249, filed on Sep. 14, 2023, the entire disclosure of which is incorporated herein by reference.

BACKGROUND

Technical Field

The present disclosure relates to an imaging control device, an imaging control method, and an imaging control program.

Related Art

In surgical operations and catheter treatment, it is necessary to ascertain a positional relationship between surgical instruments and human body structures such as bones and blood vessels. Therefore, during operation, a subject is imaged by a fluoroscopy apparatus, and the positional relationship between the surgical instrument and the human body structure is ascertained using a fluoroscopic image of radiation displayed on a display by the imaging. However, the surgical instrument and the human body structure have a three-dimensional positional relationship, whereas the fluoroscopic image is a two-dimensional image. Even in a case of viewing such a two-dimensional fluoroscopic image, it is difficult to ascertain a three-dimensional positional relationship between the surgical instrument and the human body structure.

Therefore, a fluoroscopy apparatus that comprises two sets of detection units and radiation sources and performs imaging on a subject in two directions to ascertain a three-dimensional positional relationship between a surgical instrument and a human body structure has been proposed (see JP2019-087892A). In the apparatus disclosed in JP2019-087892A, a timing of performing imaging is controlled such that a period in which the first detection unit of the two detection units is irradiated with radiation and a period in which the second detection unit thereof is irradiated with radiation do not overlap each other.

On the other hand, two fluoroscopy apparatuses are used to perform imaging on the subject in two directions.

In a case in which two fluoroscopy apparatuses are used, radiation emitted to the subject from one apparatus may be scattered by the subject, resulting in unintended radiation being detected by the other apparatus. In this case, the image quality of the fluoroscopic images acquired by both the apparatuses is degraded. Furthermore, in a case in which radiation is emitted to the subject from one apparatus while calibration is being performed by the other apparatus, unnecessary radiation may be detected during the calibration in the other apparatus, which may cause a failure in the calibration.

SUMMARY OF THE INVENTION

The present disclosure has been made in view of the above circumstances, and an object of the present disclosure is to reduce an influence of radiation emitted from another fluoroscopy apparatus in a case in which fluoroscopy is performed using a plurality of fluoroscopy apparatuses.

According to an aspect of the present disclosure, there is provided an imaging control device that controls fluoroscopy of a subject in each of a plurality of fluoroscopy apparatuses that are used simultaneously in a case in which the fluoroscopy is performed in a plurality of directions, the imaging control device comprising: at least one processor, in which the processor is configured to: mutually register another fluoroscopy apparatus other than a fluoroscopy apparatus of which the imaging control device itself controls the fluoroscopy; and notify, in a case in which an instruction to start emitting radiation is given and the radiation is emitted from the fluoroscopy apparatus of which the imaging control device itself controls the fluoroscopy, the other fluoroscopy apparatus that the radiation has been emitted.

In the imaging control device according to the aspect of the present disclosure, the processor may be configured to: set the fluoroscopy apparatus of which the imaging control device itself controls the fluoroscopy to a registration standby state; search for the other fluoroscopy apparatus in a registration standby state; and mutually register the found other fluoroscopy apparatus.

In the imaging control device according to the aspect of the present disclosure, the processor may be configured to notify, in a case in which the instruction to start emitting the radiation is given, the other fluoroscopy apparatus that the emission of the radiation has started.

In the imaging control device according to the aspect of the present disclosure, the instruction to start emitting the radiation may be given by turning on a radiation irradiation switch of the fluoroscopy apparatus, and the processor may be configured to notify the other fluoroscopy apparatus that the emission of the radiation has started by transmitting a radiation irradiation start flag to the other fluoroscopy apparatus.

In the imaging control device according to the aspect of the present disclosure, the processor may be configured to notify, in a case in which an instruction to stop emitting the radiation is given, the other fluoroscopy apparatus that the emission of the radiation has been stopped.

In the imaging control device according to the aspect of the present disclosure, the instruction to stop emitting the radiation may be given by turning off a radiation irradiation switch of the fluoroscopy apparatus, and the processor may be configured to notify the other fluoroscopy apparatus that the emission of the radiation has been stopped by transmitting a radiation irradiation stop flag to the other fluoroscopy apparatus.

In the imaging control device according to the aspect of the present disclosure, the fluoroscopy apparatus may emit the radiation in a pulsed manner, and the processor may be configured to notify the other fluoroscopy apparatus that the radiation has been emitted each time the radiation is emitted in a pulsed manner.

In the imaging control device according to the aspect of the present disclosure, the processor may be configured to perform, in a case in which a notification of the emission of the radiation from the other fluoroscopy apparatus is provided during the fluoroscopy of the subject, processing of reducing an influence of the radiation emitted from the other fluoroscopy apparatus on a fluoroscopic image acquired by the fluoroscopy.

In the imaging control device according to the aspect of the present disclosure, the processing of reducing the influence of the radiation may be scattered ray removal processing of removing a scattered ray component from the fluoroscopic image.

In the imaging control device according to the aspect of the present disclosure, the processor may be configured to perform, in a case of performing calibration of the fluoroscopy apparatus of which the imaging control device itself controls the fluoroscopy, the calibration at a timing at which a notification of the emission of the radiation from the other fluoroscopy apparatus is not provided.

In the imaging control device according to the aspect of the present disclosure, the processor may be configured to stop, in a case in which a notification of the emission of the radiation from the other fluoroscopy apparatus is provided during calibration of the fluoroscopy apparatus of which the imaging control device itself controls the fluoroscopy, the calibration.

According to another aspect of the present disclosure, there is provided an imaging control method in which a computer controls fluoroscopy of a subject in each of a plurality of fluoroscopy apparatuses that are used simultaneously in a case in which the fluoroscopy is performed in a plurality of directions, the imaging control method comprising: mutually registering another fluoroscopy apparatus other than a fluoroscopy apparatus of which the imaging control device itself controls the fluoroscopy; and notifying, in a case in which an instruction to start emitting radiation is given and the radiation is emitted from the fluoroscopy apparatus of which the imaging control device itself controls the fluoroscopy, the other fluoroscopy apparatus that the radiation has been emitted.

According to still another aspect of the present disclosure, there is provided an imaging control program causing a computer to execute processing of controlling fluoroscopy of a subject in each of a plurality of fluoroscopy apparatuses that are used simultaneously in a case in which the fluoroscopy is performed in a plurality of directions, the imaging control program comprising: a step of mutually registering another fluoroscopy apparatus other than a fluoroscopy apparatus of which the imaging control device itself controls the fluoroscopy; and a step of notifying, in a case in which an instruction to start emitting radiation is given and the radiation is emitted from the fluoroscopy apparatus of which the imaging control device itself controls the fluoroscopy, the other fluoroscopy apparatus that the radiation has been emitted.

According to the aspects of the present disclosure, it is possible to reduce an influence of radiation emitted from another fluoroscopy apparatus in a case in which fluoroscopy is performed using a plurality of fluoroscopy apparatuses.

DETAILED DESCRIPTION

Figure 1:
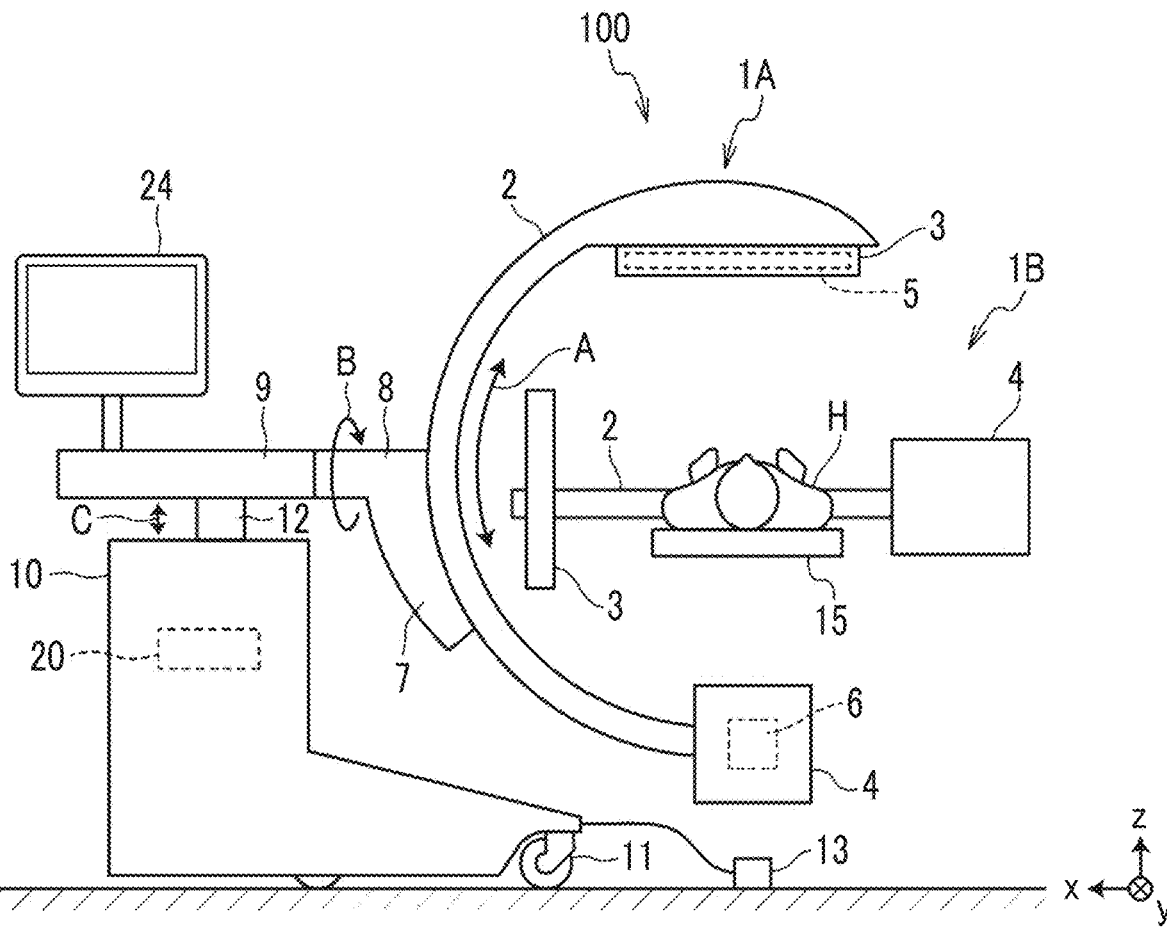
FIG. 1 is a diagram showing an overview of a fluoroscopy system including a plurality of fluoroscopy apparatuses each equipped with an imaging control device according to an embodiment of the present disclosure.

Hereinafter, embodiments of the present disclosure will be described with reference to the drawings. FIG. 1 is a schematic block diagram showing a configuration of a fluoroscopy system including a plurality of fluoroscopy apparatuses each equipped with an imaging control device according to an embodiment of the present disclosure. As shown in FIG. 1, a fluoroscopy system 100 according to the present embodiment comprises first and second fluoroscopy apparatuses 1A and 1B that are used simultaneously.

As shown in FIG. 1, the first fluoroscopy apparatus 1A according to the present embodiment comprises a C-arm 2. A detection unit 3 is attached to one end part of the C-arm 2, and a radiation emitting unit 4 is attached to the other end part of the C-arm 2 to face the detection unit 3. The second fluoroscopy apparatus 1B has a configuration similar to that of the first fluoroscopy apparatus 1A. However, only the C-arm 2, the detection unit 3, and the radiation emitting unit 4 are shown in FIG. 1, and other components are not shown.

Figure 2A:
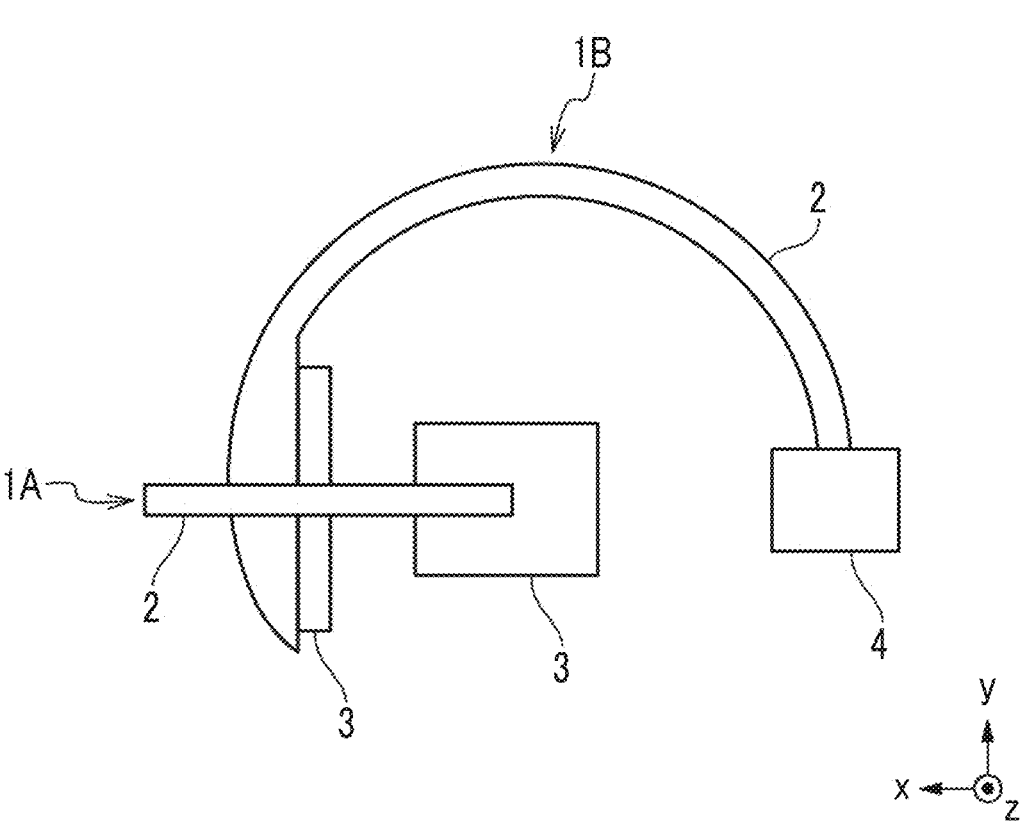
FIGS. 2A and 2B are diagrams showing a positional relationship between first and second fluoroscopy apparatuses.
Figure 2B:
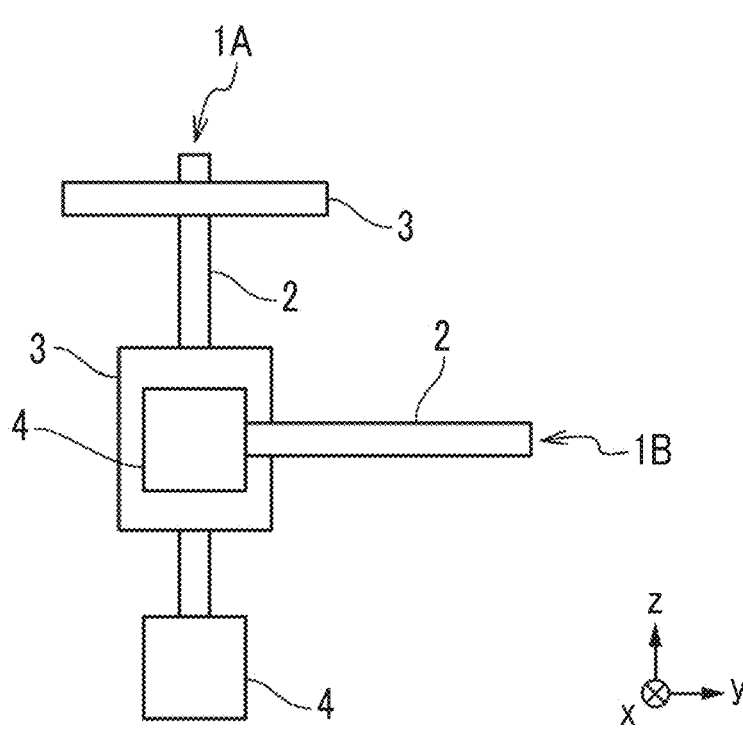

FIGS. 2A and 2B are diagrams showing a positional relationship between the first and second fluoroscopy apparatuses 1A and 1B. In the present embodiment, it is assumed that an x-axis is set in a left-right direction of FIG. 1, a y-axis is set in a depth direction of FIG. 1, and a z-axis is set in a direction perpendicular to a surface on which the first and second fluoroscopy apparatuses 1A and 1B shown in FIG. 1 are placed. FIG. 2A shows a state in which the fluoroscopy system 100 is viewed in the z direction, and FIG. 2B shows a state in which the fluoroscopy system 100 is viewed in the x direction. In the states shown in FIGS. 1 to 2B, the first fluoroscopy apparatus 1A is disposed to capture an image of a subject H in the z direction, and the second fluoroscopy apparatus 1B is disposed to capture an image of the subject H in the x direction.

The configuration of the first fluoroscopy apparatus 1A will be described below in detail. Since the configuration of the second fluoroscopy apparatus 1B is the same as the configuration of the first fluoroscopy apparatus 1A, a detailed description of the second fluoroscopy apparatus 1B will be omitted.

A radiation detector 5, such as a flat panel detector, is provided in the detection unit 3. In addition, for example, a circuit board including a charge amplifier that converts a charge signal read out from the radiation detector 5 into a voltage signal, a sampling two correlation pile circuit that samples the voltage signal output from the charge amplifier, and an analog-digital (AD) conversion unit that converts the voltage signal into a digital signal is also provided in the detection unit 3. Further, in the present embodiment, the radiation detector 5 is used. On the other hand, the present embodiment is not limited to the radiation detector 5 as long as radiation can be detected and the radiation can be converted into an image. For example, a detection device such as an image intensifier can be used.

The radiation detector 5 can repeatedly perform recording and reading out of a radiation image, may be a so-called direct-type radiation detector that directly converts radiation such as X-rays into charges, or may be a so-called indirect-type radiation detector that converts radiation into visible light once and converts the visible light into a charge signal. As a method for reading out a radiation image signal, it is desirable to use the following method: a so-called thin film transistor (TFT) readout method which reads out a radiation image signal by turning on and off a TFT switch; or a so-called optical readout method which reads out a radiation image signal by irradiating a target with readout light. On the other hand, the readout method is not limited thereto, and other methods may be used.

A radiation source 6 is accommodated in the radiation emitting unit 4, and the radiation source 6 emits radiation toward the detection unit 3. The radiation source 6 emits X-rays as radiation, and a timing at which the radiation source 6 emits radiation and a timing at which the radiation detector 5 detects the radiation are controlled by an imaging controller, which will be described later. In addition, the radiation generation conditions in the radiation source 6, that is, the selection of the material of the target and the filter, the tube voltage, the irradiation time, and the like are also controlled by the imaging controller.

The C-arm 2 according to the present embodiment is held by a C-arm holding part 7 to be movable in the direction of an arrow A shown in FIG. 1, and integrally changeable in angle with respect to the detection unit 3 and the radiation emitting unit 4 in the z direction (vertical direction) shown in FIG. 1. In addition, the C-arm holding part 7 includes a shaft part 8, and the shaft part 8 rotatably connects the C-arm 2 to a bearing 9. Thereby, the C-arm 2 is configured to be rotatable in the direction of an arrow B shown in FIG. 1 with the shaft part 8 as a rotation axis.

In addition, as shown in FIG. 1, the first fluoroscopy apparatus 1A comprises a body part 10. A plurality of wheels 11 are attached to a bottom portion of the body part 10, and thus, the first fluoroscopy apparatus 1A can be moved. A support shaft 12 that is expanded and contracted in a z-axis direction of FIG. 1 is provided on an upper portion side of a housing of the body part 10 in FIG. 1. The bearing 9 is held on the upper portion of the support shaft 12 to be movable in the direction of an arrow C.

In addition, a foot switch 13 for turning on and off the emission of radiation from the radiation source 6 of the radiation emitting unit 4 is connected to the body part 10. In a case in which a doctor during operation steps on the foot switch 13, it is turned on, and as a result, radiation is emitted from the radiation source 6. In a case in which the doctor removes his/her foot from the foot switch 13, it is turned off, and as a result, the emission of the radiation from the radiation source 6 is stopped. The foot switch 13 is an example of a radiation irradiation switch.

The first fluoroscopy apparatus 1A has the above-described configuration, and thus, irradiates the subject H from below the subject H who is lying on an imaging table 15 with radiation, detects the radiation transmitted through the subject H with the radiation detector 5 of the detection unit 3, and acquires a fluoroscopic image of the subject H from the front. On the other hand, the second fluoroscopy apparatus 1B irradiates the subject H from the side of the subject H who is lying on the imaging table 15 with radiation, detects the radiation transmitted through the subject H with the radiation detector 5 of the detection unit 3, and acquires a fluoroscopic image of the subject H from the side. By displaying the two fluoroscopic images thus acquired with different imaging directions, it is possible to ascertain the state of the inside of the subject H in a three-dimensional manner.

Here, the C-arm 2 is movable in the direction of the arrow A, the direction of the arrow B, and the direction of the arrow C, and the first and second fluoroscopy apparatuses 1A and 1B are movable by the wheels 11. Therefore, the first and second fluoroscopy apparatuses 1A and 1B can image a desired part of the subject H who is lying on the imaging table 15 in a desired direction while adjusting their own positions and the position of the C-arm 2.

Figure 3:
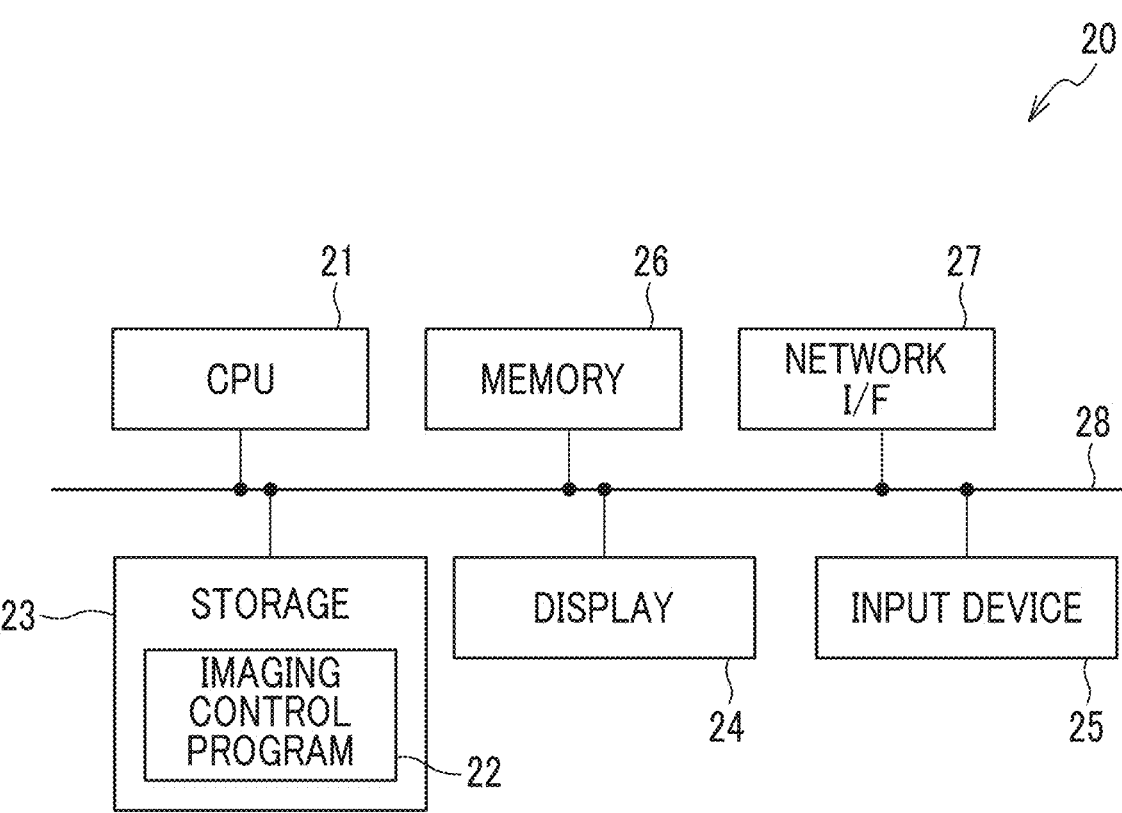
FIG. 3 is a diagram showing a schematic configuration of the imaging control device according to the present embodiment.

The body part 10 is provided with an imaging control device 20 according to the present embodiment for controlling the imaging of the first and second fluoroscopy apparatuses 1A and 1B. FIG. 3 is a diagram showing a hardware configuration of the imaging control device. As shown in FIG. 3, the imaging control device 20 is a computer, such as a workstation, a server computer, and a personal computer, and comprises a central processing unit (CPU) 21, a non-volatile storage 23, and a memory 26 as a temporary storage area. In addition, the imaging control device 20 comprises a display 24, such as a liquid crystal display, an input device 25 such as a keyboard and a mouse, and a wired or wireless interface (I/F) 27 that is connected to the detection unit 3, the radiation emitting unit 4, and the foot switch 13, and is used to exchange information with external devices. The CPU 21, the storage 23, the display 24, the input device 25, the memory 26, and the I/F 27 are connected to a bus 28. The CPU 21 is an example of a processor according to the present disclosure.

The storage 23 is realized by a hard disk drive (HDD), a solid-state drive (SSD), a flash memory, and the like. An imaging control program 22 installed in the imaging control device 20 is stored in the storage 23 serving as a storage medium. The CPU 21 reads out the imaging control program 22 from the storage 23, loads the imaging control program 22 into the memory 26, and executes the loaded imaging control program 22.

The imaging control program 22 is stored in a storage device of a server computer connected to the network or in a network storage in a state in which it can be accessed from the outside, and is downloaded to and installed on the imaging control device 20 in response to a request. Alternatively, the imaging control program 22 is recorded on a recording medium, such as a digital versatile disc (DVD) and a compact disc read-only memory (CD-ROM), and distributed, and is installed on the imaging control device 20 from the recording medium.

Figure 4:
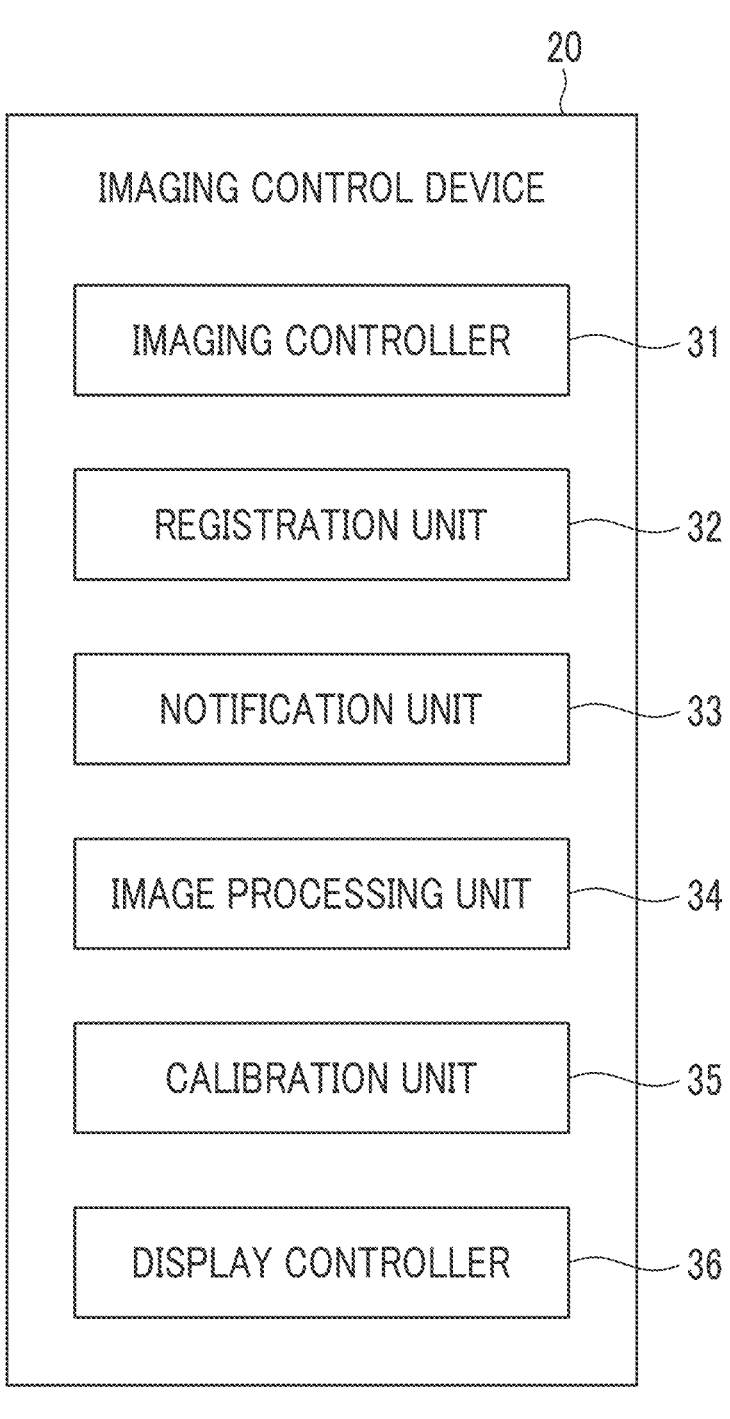
FIG. 4 is a diagram showing a functional configuration of the imaging control device according to the present embodiment.

Next, a functional configuration of the imaging control device according to the present embodiment will be described. FIG. 4 is a diagram showing a functional configuration of the imaging control device according to the present embodiment. As shown in FIG. 4, the imaging control device 20 comprises an imaging controller 31, a registration unit 32, a notification unit 33, an image processing unit 34, a calibration unit 35, and a display controller 36. Then, the CPU 21 executes the imaging control program 22, whereby the CPU 21 functions as the imaging controller 31, the registration unit 32, the notification unit 33, the image processing unit 34, the calibration unit 35, and the display controller 36.

In a case in which the foot switch 13 is turned on and an on signal from the foot switch 13 is input, the imaging controller 31 causes radiation to be emitted from the radiation source 6 included in the radiation emitting unit 4 based on imaging conditions set by a console (not shown). Furthermore, the imaging controller 31 detects the radiation transmitted through the subject H with the radiation detector 5 of the detection unit 3 in response to the timing at which the radiation is emitted from the radiation source 6, and generates a fluoroscopic image of the subject H. The generated fluoroscopic image is displayed on the display 24.

In the present embodiment, the imaging controller 31 controls the radiation source 6 to emit the radiation in a pulsed manner while the foot switch 13 is turned on. Accordingly, the pulsed radiation is emitted from the radiation source 6, and the fluoroscopic image is generated by the radiation detector 5 at a timing corresponding to the emission of the radiation. Therefore, the fluoroscopic images are continuously displayed on the display 24 like a moving image at a timing corresponding to the emission of the pulsed radiation.

The registration unit 32 mutually registers a fluoroscopy apparatus other than the fluoroscopy apparatus of which the imaging control device 20 itself controls the fluoroscopy. Specifically, the registration unit 32 performs pairing with a fluoroscopy apparatus other than the fluoroscopy apparatus of which the imaging control device 20 itself controls the fluoroscopy. In the present embodiment, the registration unit 32 of the first fluoroscopy apparatus 1A performs pairing with the second fluoroscopy apparatus 1B, and the registration unit 32 of the second fluoroscopy apparatus 1B performs pairing with the first fluoroscopy apparatus 1A.

For the pairing, for example, a method similar to that of short-range wireless communication, such as Bluetooth (registered trademark), may be used. That is, pairing may be performed by making the first fluoroscopy apparatus 1A and the second fluoroscopy apparatus 1B recognize each other, and giving an instruction to perform pairing via the input device 25.

At the time of registration, a user such as a doctor or a medical assistant performs an operation for putting the apparatus itself into a registration standby state using the input device 25 for each of the first fluoroscopy apparatus 1A and the second fluoroscopy apparatus 1B. Accordingly, the registration unit 32 sets the fluoroscopy apparatus provided therein to a registration standby state. Next, the registration unit 32 searches for another fluoroscopy apparatus in the registration standby state. For example, in the present embodiment, since both the first and second fluoroscopy apparatuses 1A and 1B are set to a registration standby state, in a case in which the registration unit 32 of the imaging control device 20 of the first fluoroscopy apparatus 1A searches for an apparatus in a registration standby state, the second fluoroscopy apparatus 1B is found. On the other hand, in a case in which the registration unit 32 of the imaging control device 20 of the second fluoroscopy apparatus 1B searches for an apparatus in a registration standby state, the first fluoroscopy apparatus 1A is found.

The registration unit 32 of the imaging control device 20 of the first fluoroscopy apparatus 1A performs pairing with the found second fluoroscopy apparatus 1B, and mutually registers the found second fluoroscopy apparatus 1B. The registration unit 32 of the imaging control device 20 of the second fluoroscopy apparatus 1B performs pairing with the found first fluoroscopy apparatus 1A, and mutually registers the found first fluoroscopy apparatus 1A.

In a case in which the imaging controller 31 causes the radiation source 6 to emit radiation, the notification unit 33 notifies the other mutually registered fluoroscopy apparatus that radiation has been emitted. That is, in a case in which radiation is emitted from the radiation source 6 of the first fluoroscopy apparatus 1A, the notification unit 33 of the imaging control device 20 of the first fluoroscopy apparatus 1A notifies the second fluoroscopy apparatus 1B that the radiation has been emitted. In a case in which radiation is emitted from the radiation source 6 of the second fluoroscopy apparatus 1B, the notification unit 33 of the imaging control device 20 of the second fluoroscopy apparatus 1B notifies the first fluoroscopy apparatus 1A that the radiation has been emitted. A notification is performed through short-range wireless communication.

Figure 5:
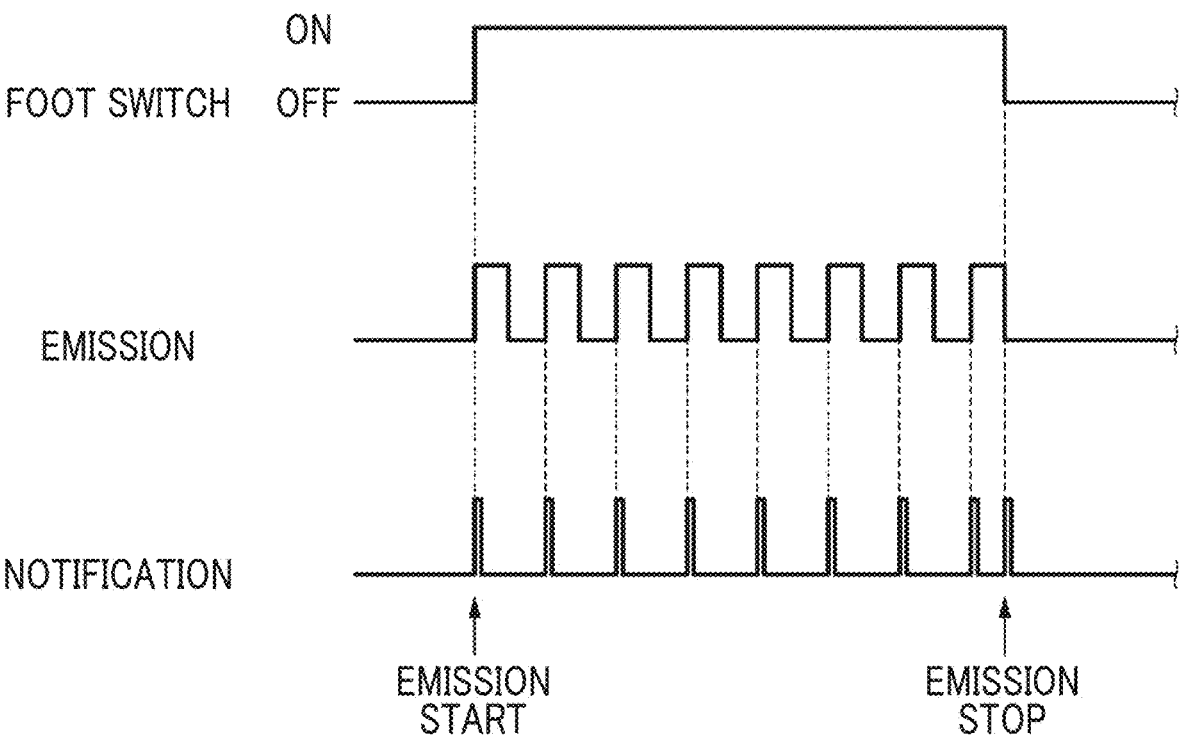
FIG. 5 is a diagram for describing a timing of a notification.

FIG. 5 is a diagram for describing a timing of a notification. The horizontal axis in FIG. 5 represents time, and shows the on/off of the foot switch 13, the timing of the radiation emitted from the radiation source 6, and the timing of receiving a notification in order from the top to bottom. As shown in FIG. 5, in the present embodiment, in a case in which the foot switch 13 is turned on from the off state, radiation is emitted from the radiation source 6 in a pulsed manner. The notification unit 33 transmits a flag for starting radiation irradiation to the other mutually registered fluoroscopy apparatus at a timing at which the foot switch 13 is turned on.

Further, the notification unit 33 transmits a flag for notifying the other mutually registered fluoroscopy apparatus of the emission of the radiation at a timing at which the radiation is emitted in a pulsed manner.

The flag that is first transmitted after the foot switch 13 is turned on indicates both the start of radiation emission and that radiation has been emitted. Accordingly, the other mutually registered fluoroscopy apparatus is notified of the start of radiation emission and the timing at which the radiation has been emitted in a pulsed manner.

On the other hand, in a case in which the foot switch 13 is turned off, the emission of the radiation is stopped, and the notification unit 33 transmits a flag indicating that the emission of the radiation has been stopped to the other mutually registered fluoroscopy apparatus. Accordingly, the other mutually registered fluoroscopy apparatus is notified of the stop of the radiation irradiation. Thereafter, the notification unit 33 stops the notification.

In a case in which a notification of radiation emission from another fluoroscopy apparatus other than itself is provided and fluoroscopy of the subject H is performed in the own fluoroscopy apparatus, that is, in a case in which the fluoroscopy is performed simultaneously in both the first and second fluoroscopy apparatuses 1A and 1B, the image processing unit 34 performs processing of reducing an influence of the radiation emitted from the other fluoroscopy apparatus on the fluoroscopic image acquired by the fluoroscopy.

Specifically, in a case in which a notification of radiation emission from the second fluoroscopy apparatus 1B is provided and fluoroscopy of the subject H is performed in the first fluoroscopy apparatus 1A, the image processing unit 34 of the imaging control device 20 of the first fluoroscopy apparatus 1A performs processing of reducing an influence of the radiation emitted from the second fluoroscopy apparatus 1B on the fluoroscopic image acquired by the fluoroscopy. In this case, the image processing unit 34 of the imaging control device 20 of the second fluoroscopy apparatus 1B performs processing of reducing the influence of the radiation emitted from the first fluoroscopy apparatus 1A on the acquired fluoroscopic image.

Examples of the processing of reducing the influence of the radiation include scattered ray removal processing of removing a scattered ray component from the fluoroscopic image. In the present embodiment, the image processing unit 34 removes a scattered ray component from a fluoroscopic image 1 using, for example, methods disclosed in JP2014-207958A, JP2015-043959A, and the like. The method of removing the scattered ray component is not limited thereto, and any method can be used. In the following, scattered ray removal processing in a case in which the method disclosed in JP2015-043959A is used will be described. In a case in which a method disclosed in JP2015-043959A or the like is used, the derivation of the body thickness distribution of the subject H and the derivation of the scattered ray component for removing the scattered ray component are performed simultaneously.

In the case of removing the scattered ray component, a low frequency image representing a low frequency component of the fluoroscopic image may be generated, and the body thickness distribution may be derived using the low frequency image.

First, the image processing unit 34 acquires a virtual model K1 of the subject H having an initial body thickness distribution Ts(x, y). The virtual model K1 is data for virtually representing the subject H, in which the body thickness according to the initial body thickness distribution Ts(x, y) is associated with the coordinate position of each pixel of the fluoroscopic image. In addition, the virtual model K1 of the subject H having the initial body thickness distribution Ts(x, y) is stored in the storage 23 in advance. However, the virtual model K1 may be acquired from an external server storing the virtual model K1.

Then, the image processing unit 34 derives an estimated primary ray image Ip(x, y) which is obtained by estimating a primary ray image obtained by capturing the image of the virtual model K1 and an estimated scattered ray image Is(x, y) which is obtained by estimating a scattered ray image obtained by capturing the image of the virtual model K1, based on the virtual model K1, as represented by the following Expressions (1) and (2). Further, as represented by the following Expression (3), the image processing unit 34 derives a composite image of the estimated primary ray image Ip(x, y) and the estimated scattered ray image Is(x, y) as an estimated image Im(x, y) which is obtained by estimating the fluoroscopic image obtained by capturing the image of the subject H.

$$Ip(x, y) = Io(x, y) \times \exp(-\mu ls \times T(x, y)) \quad (1)$$

$$Is(x, y) = Io(x, y) * So(T(x, y)) \quad (2)$$

$$Im(x, y) = Is(x, y) + Ip(x, y) \quad (3)$$

Here, (x, y) is the coordinate of the pixel position of the fluoroscopic image, Ip(x, y) is a primary ray component at the pixel position (x, y), Is(x, y) is a scattered ray component at the pixel position (x, y), Io(x, y) is an incident dose on the surface of the subject H at the pixel position (x, y), $\mu ls$ is an attenuation coefficient of the subject H, and $So(T(x, y))$ is a convolutional kernel indicating scattering characteristics corresponding to the body thickness distribution T(x, y) of the subject H at the pixel position (x, y). Note that, in a case of deriving the first estimated image Im(x, y), the initial body thickness distribution Ts(x, y) is used as the body thickness distribution T(x, y) in Expressions (1) and (2). Expression (1) is based on a known exponential attenuation law, and Expression (2) is based on the method disclosed in "JM Boon et al, An analytical model of the scattered radiation distribution in diagnostic radiology, Med. Phys. 15 (5), September/October 1988 (Reference Literature 1). The incident dose Io(x, y) on the surface of the subject H is an irradiation dose that is derived based on the imaging conditions. Furthermore, the attenuation coefficient $\mu ls$ of the subject H in Expression (1) is the attenuation coefficient of the soft tissue in the low-energy image of the subject H.

Further, * in Expression (2) is an operator indicating a convolution operation. The properties of the kernel change not only depending on the body thickness of the subject H, but also depending on the distribution of the irradiation field in the fluoroscopy apparatuses 1A and 1B, the distribution of the composition of the subject H, the irradiation dose at the time of imaging, the tube voltage, the imaging distance, the characteristics of the radiation detector 5 used in the detection unit 3, and the like. According to the method disclosed in Reference Literature 1, the scattered rays can be approximated by the convolution of a point spread function ($So(T(x, y))$ in Expression (2)) for the primary rays. Note that, $So(T(x, y))$ can be experimentally calculated according to, for example, irradiation field information, subject information, and imaging conditions.

In the present embodiment, $So(T(x, y))$ may be calculated based on irradiation field information, subject information, and imaging conditions at the time of imaging. However, a table in which various types of irradiation field information, various types of subject information, and various imaging conditions are associated with $So(T(x, y))$ may be stored in the storage 23, and $So(T(x, y))$ may be calculated based on the irradiation field information, the subject information, and the imaging conditions at the time of imaging with reference to the table. Incidentally, $So(T(x, y))$ may be approximated by T(x, y).

Next, the image processing unit 34 corrects the initial body thickness distribution Ts(x, y) of the virtual model K1 such that the difference between the estimated image Im and the fluoroscopic image is reduced. The image processing unit 34 repeats the generation of the estimated image Im using the corrected body thickness distribution T(x, y) and the correction of the body thickness distribution T(x, y) until the difference between the estimated image Im and the fluoroscopic image satisfies a predetermined end condition. The image processing unit 34 subtracts the scattered ray component Is(x, y) derived by Expression (3) in a case in which the end condition is satisfied from the fluoroscopic image. Accordingly, the scattered ray component included in the fluoroscopic image is removed.

The calibration unit 35 calibrates the fluoroscopy apparatus provided therein. Here, in the radiation detector 5 included in the first and second fluoroscopy apparatuses 1A and 1B, the dark current, the sensitivity, and the like are changed due to changes in the surrounding environment (temperature, humidity, and the like) or an aging change. Accordingly, the signal value output from the radiation detector 5 changes. The calibration unit 35 irradiates the radiation detector 5 with radiation from the radiation source 6 without the subject H being provided, and acquires the data output from the radiation detector 5 as calibration data for compensating for changes in the signal value output by the radiation detector 5. The processing of acquiring the calibration data in this manner is calibration. The calibration data thus acquired is used to correct the fluoroscopic images acquired by the first and second fluoroscopy apparatuses 1A and 1B.

The calibration unit 35 performs calibration at a timing at which a notification of radiation emission from another mutually registered fluoroscopy apparatus is not provided. That is, the calibration unit 35 of the imaging control device 20 of the first fluoroscopy apparatus 1A performs calibration at a timing at which a notification of radiation emission from the second fluoroscopy apparatus 1B is not provided. In addition, the calibration unit 35 of the imaging control device 20 of the second fluoroscopy apparatus 1B performs calibration at a timing at which a notification of radiation emission from the first fluoroscopy apparatus 1A is not provided.

In a case in which a notification of radiation emission from another fluoroscopy apparatus is provided during the calibration, the calibration unit 35 stops the calibration. That is, in a case in which a notification of radiation emission from the second fluoroscopy apparatus 1B is provided during calibration, the calibration unit 35 of the imaging control device 20 of the first fluoroscopy apparatus 1A stops the calibration. In a case in which a notification of radiation emission from the first fluoroscopy apparatus 1A is provided during calibration, the calibration unit 35 of the imaging control device 20 of the second fluoroscopy apparatus 1B stops the calibration.

Figure 6:
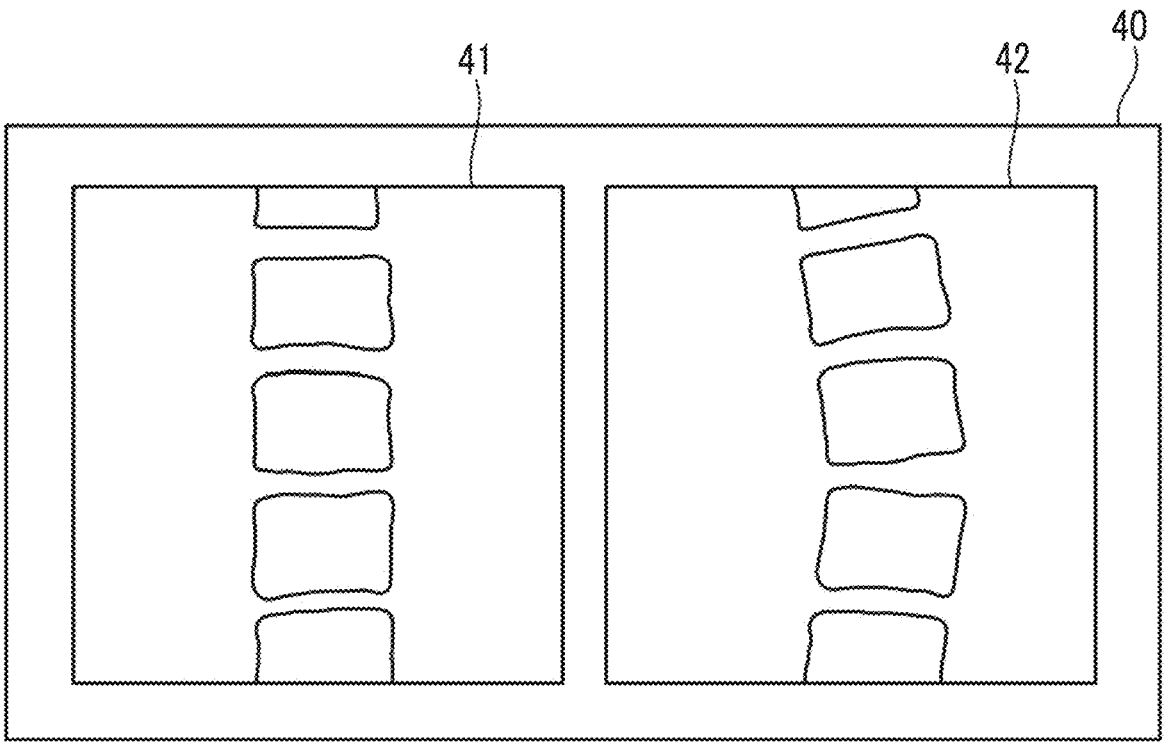
FIG. 6 is a diagram showing a display screen of fluoroscopic images.

The display controller 36 displays the fluoroscopic images acquired by the first and second fluoroscopy apparatuses 1A and 1B on the display 24. FIG. 6 is a diagram showing a display screen of fluoroscopic images. As shown in FIG. 6, a fluoroscopic image 41 acquired by the first fluoroscopy apparatus 1A and a fluoroscopic image 42 acquired by the second fluoroscopy apparatus 1B are displayed side by side on a display screen 40. The fluoroscopic image 41 is a front image of the subject H, and the fluoroscopic image 42 is a side image of the subject H. Although it is preferable that the two fluoroscopic images 41 and 42 are displayed side by side on the display 24 of both of the fluoroscopy apparatuses 1A and 1B, they may be displayed side by side on the display 24 of either one of the fluoroscopy apparatuses 1A and 1B.

Figure 7:
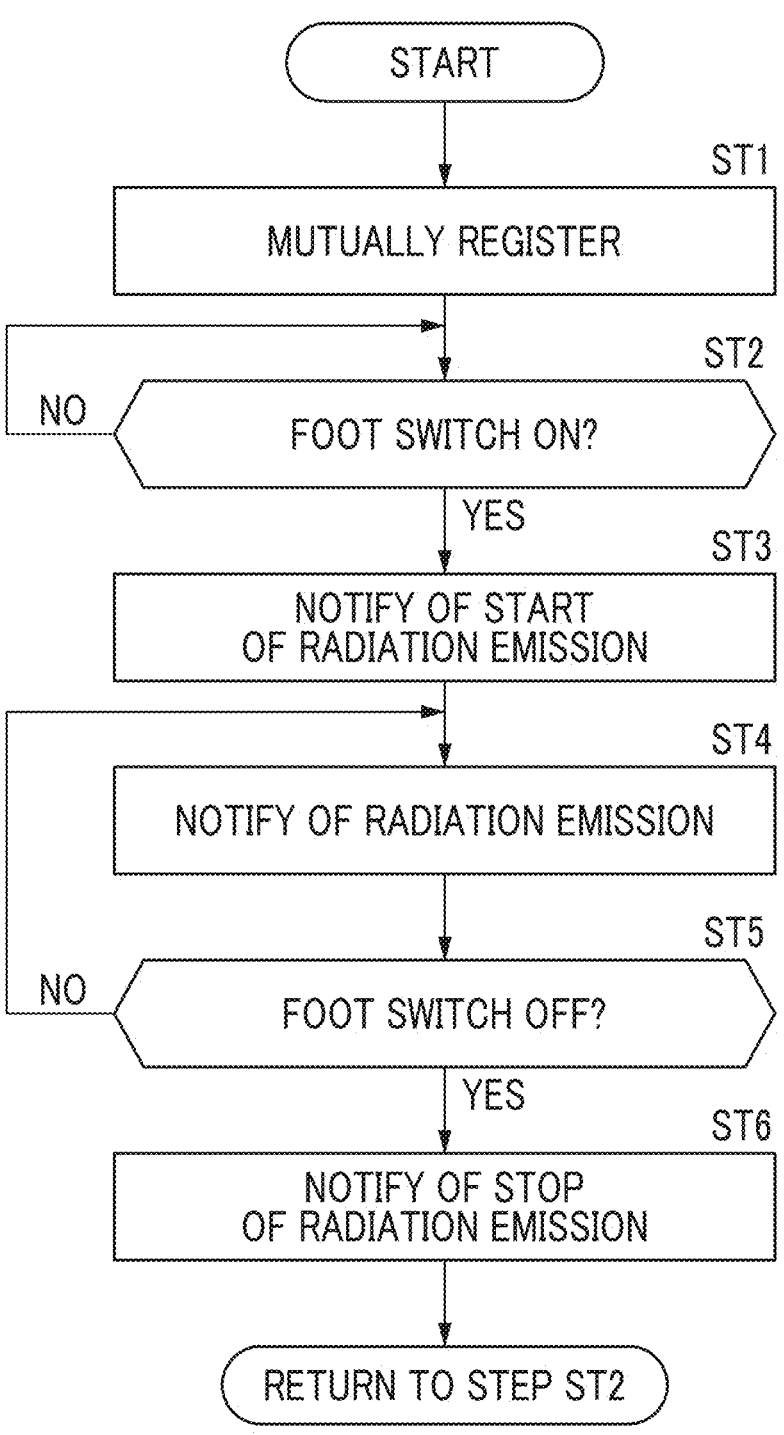
FIG. 7 is a flowchart showing radiation emission notification processing performed in the present embodiment.

Next, processing performed in the present embodiment will be described. FIG. 7 is a flowchart showing radiation emission notification processing. FIG. 7 shows only the processing performed in one of the first fluoroscopy apparatus 1A and the second fluoroscopy apparatus 1B. First, the registration unit 32 performs pairing to mutually register the first fluoroscopy apparatus 1A and the second fluoroscopy apparatus 1B (Step ST1).

Figure 8:
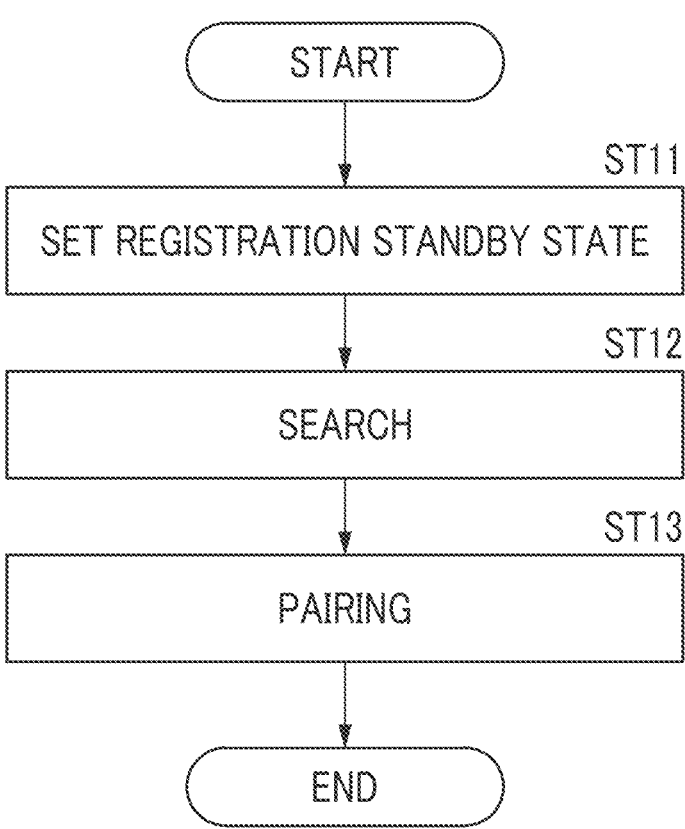
FIG. 8 is a flowchart showing registration processing performed in the present embodiment.

FIG. 8 is a flowchart showing mutual registration processing. The registration unit 32 sets the fluoroscopy apparatus provided therein to a registration standby state (Step ST11). Next, the registration unit 32 searches for another fluoroscopy apparatus in the registration standby state (Step ST12). Then, the registration unit 32 performs pairing with the found other fluoroscopy apparatus (Step ST13), thereby mutually registering the found other fluoroscopy apparatus, and ends the mutual registration processing.

Referring back to FIG. 7, next, the imaging controller 31 starts monitoring whether or not an instruction to start emitting radiation has been given by turning on the foot switch 13 (Step ST2). In a case in which a determination result in Step ST2 is "Yes", the notification unit 33 notifies of the start of the radiation emission (Step ST3), and further notifies of the radiation emission at the timing at which the radiation is emitted from the radiation source 6 (Step ST4). Next, the imaging controller 31 starts monitoring whether or not an instruction to stop the radiation emission has been given by turning off the foot switch 13 (Step ST5), and then, in a case in which a determination result in Step ST5 is "No", the process returns to Step ST4. In a case in which the determination result in Step ST5 is "Yes", the notification unit 33 notifies of the stop of the radiation emission (Step ST6), and the process returns to Step ST2.

Figure 9:
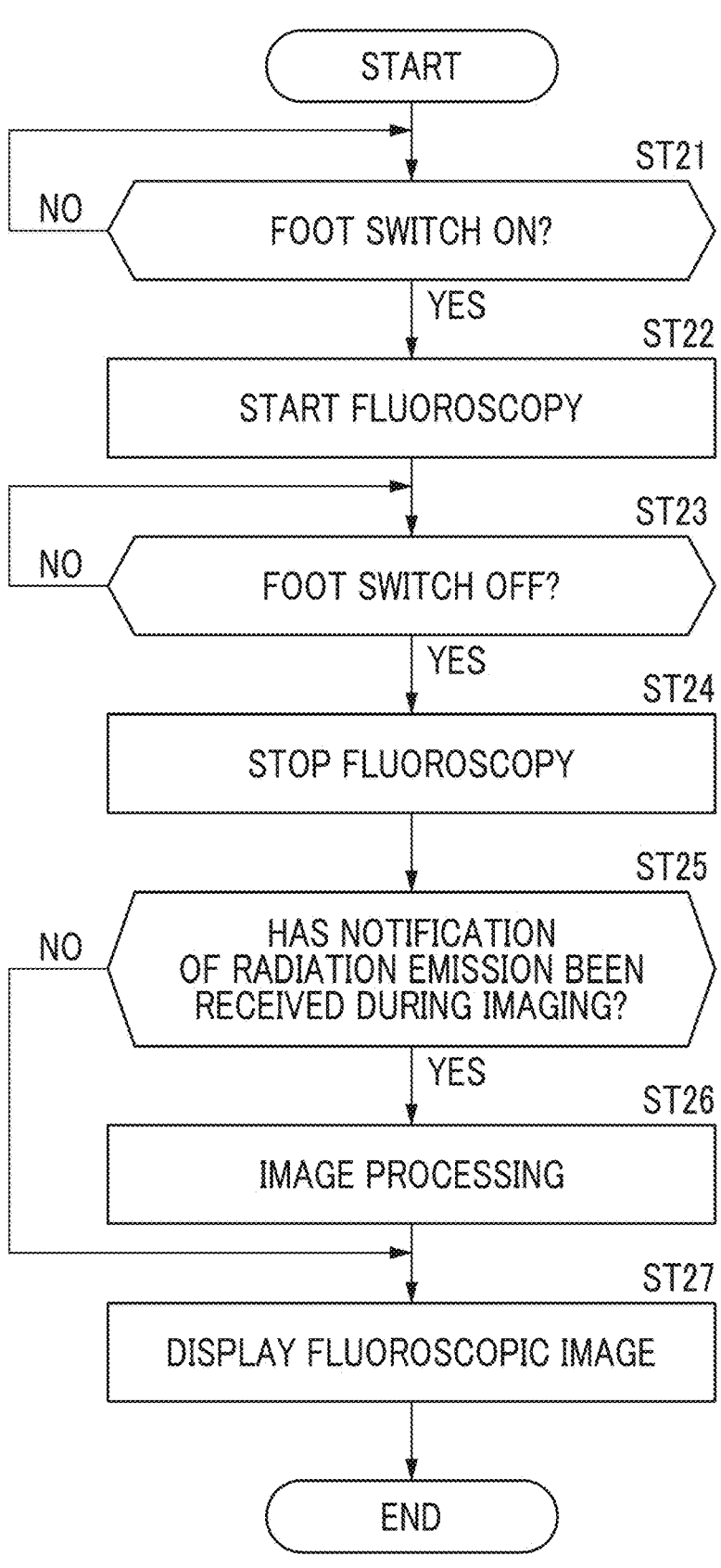
FIG. 9 is a flowchart showing image processing performed in the present embodiment.

FIG. 9 is a flowchart showing image processing performed in the present embodiment. It is assumed that the mutual registration of the first and second fluoroscopy apparatuses 1A and 1B has been completed. First, the imaging controller 31 starts monitoring whether or not an instruction to start emitting radiation has been given by turning on the foot switch 13 (Step ST21). In a case in which a determination result in Step ST21 is "Yes", the imaging controller 31 emits the radiation from the radiation source 6 to start the fluoroscopy of the subject H (Step ST22). Next, the imaging controller 31 starts monitoring whether or not an instruction to stop the radiation emission has been given by turning off the foot switch 13 (Step ST23), and then, in a case in which a determination result in Step ST23 is "Yes", the imaging controller 31 stops the fluoroscopy (Step ST24).

Next, the imaging controller 31 determines whether or not a notification of radiation emission has been received from another fluoroscopy apparatus during the imaging (Step ST25). In a case in which a determination result in Step ST25 is "Yes", the image processing unit 34 performs image processing (scattered ray removal processing) on the acquired fluoroscopic image (Step ST26). Then, the display controller 36 displays the fluoroscopic image on the display 24 (Step ST27), and the process ends. In a case in which the determination result in Step ST25 is "No", the image processing unit 34 does not perform any processing, the fluoroscopic image acquired in the processing of Step ST27 is displayed on the display 24, and the process ends.

Figure 10:
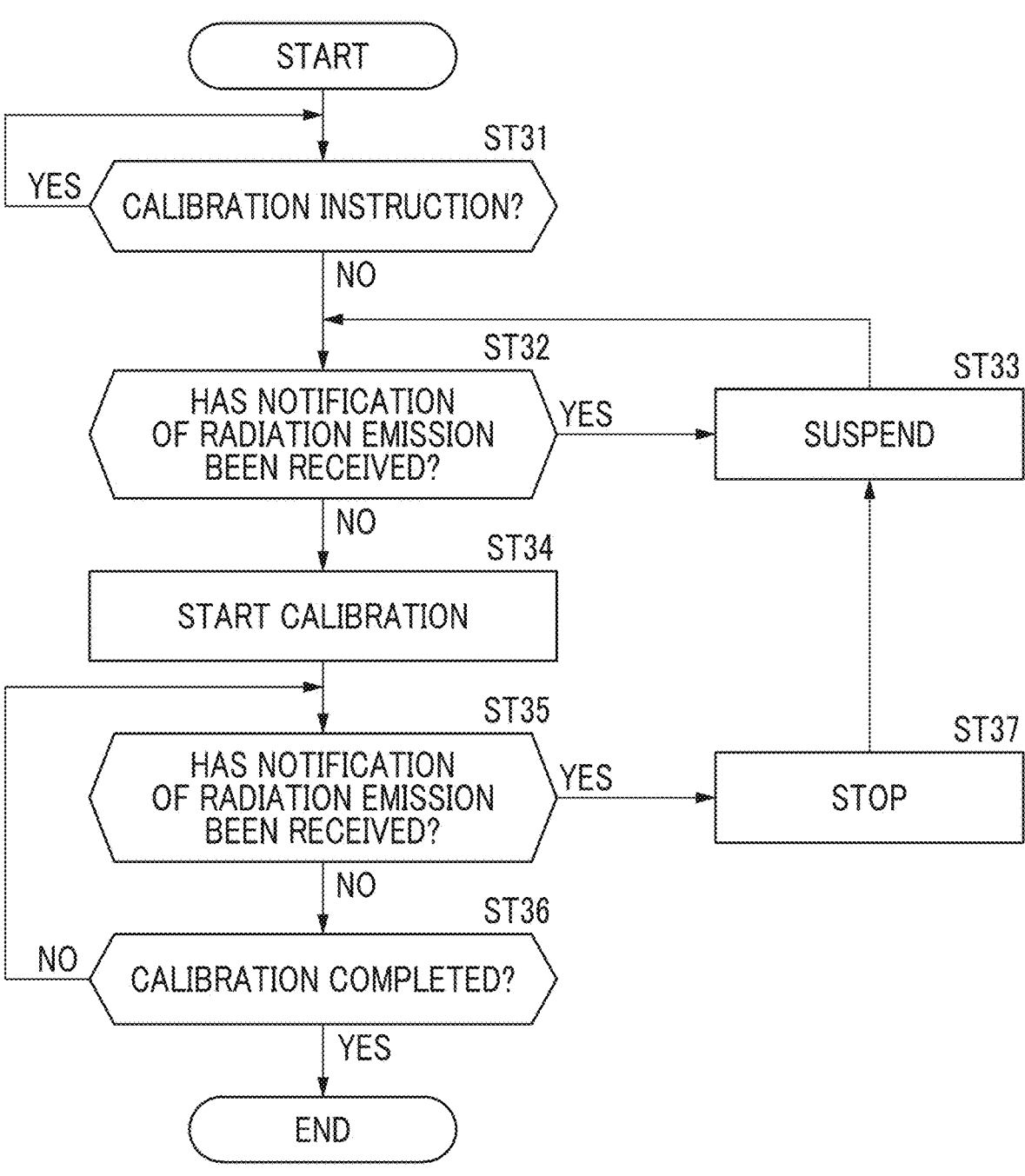
FIG. 10 is a flowchart showing processing related to calibration performed in the present embodiment.

FIG. 10 is a flowchart showing processing related to calibration performed in the present embodiment. First, the calibration unit 35 monitors whether or not a calibration instruction has been given (Step ST31). In a case in which a determination result in Step ST31 is "Yes", the calibration unit 35 determines whether or not a notification of radiation emission has been received from another fluoroscopy apparatus (Step ST32). In a case in which a determination result in Step ST32 is "Yes", the calibration unit 35 suspends the calibration processing (Step ST33), and returns to Step ST32.

In a case in which the determination result in Step ST32 is "No", the calibration unit 35 starts calibration (Step ST34). Furthermore, the calibration unit 35 determines whether or not a notification of radiation emission has been received from another fluoroscopy apparatus (Step ST35). In a case in which a determination result in Step ST35 is "No", the calibration unit 35 determines whether or not the calibration is completed (Step ST36), and in a case in which a determination result in Step ST36 is "Yes", the process ends. In a case in which the determination result in step ST36 is "No", the process returns to step ST35. In a case in which the determination result in Step ST35 is "Yes", the calibration unit 35 stops the calibration (Step ST37) and proceeds to the process of Step ST33, and the calibration unit 35 suspends the calibration processing and returns to the process of Step ST32.

In this way, in the present embodiment, in a case in which a plurality of fluoroscopy apparatuses are simultaneously used to perform fluoroscopy of a subject in a plurality of directions, the plurality of fluoroscopy apparatuses are mutually registered, and in a case in which radiation is emitted, the other fluoroscopy apparatus receives a notification of the radiation emission. Therefore, the other fluoroscopy apparatus that has received the notification can perform various processes while taking into consideration the influence of the radiation emitted by the fluoroscopy apparatus that has provided the notification. Therefore, in a case where fluoroscopy is performed using a plurality of fluoroscopy apparatuses, the influence of radiation emitted from the other fluoroscopy apparatus can be reduced.

In particular, in the present embodiment, in a case in which a notification of radiation emission from another fluoroscopy apparatus other than itself is provided and fluoroscopy of the subject H is performed in the own fluoroscopy apparatus, processing of reducing an influence of the radiation emitted from the other fluoroscopy apparatus on the fluoroscopic image acquired by the fluoroscopy, for example, scattered ray removal processing is performed. Therefore, in the acquired fluoroscopic image, it is possible to remove the influence of the scattered rays generated by the radiation emitted from the other fluoroscopy apparatus, and it is thus possible to improve the image quality of the acquired fluoroscopic image.

Furthermore, in the case of performing calibration, the calibration is performed at a timing at which a notification of radiation emission from another fluoroscopy apparatus is not provided. In addition, in a case in which a notification of radiation emission from another fluoroscopy apparatus is provided during the calibration, the calibration is stopped. This makes it possible to prevent that the calibration cannot be accurately performed due to the influence of the radiation from the other fluoroscopy apparatus.

In the above embodiment, an example in which two fluoroscopy apparatuses 1A and 1B are used has been described. However, it goes without saying that the technology of the present disclosure can be applied even in a case in which three or more fluoroscopy apparatuses are used.

In addition, in the above embodiment, the radiation source 6 emits the radiation in a pulsed manner, but the present disclosure is not limited thereto. Radiation may be continuously emitted while the foot switch 13 is turned on. In this case, the notification unit 33 may continuously notify the other fluoroscopy apparatus that radiation is being emitted.

Moreover, the radiation in each of the embodiments described above is not particularly limited, and α-rays or γ-rays can be applied in addition to X-rays.

Further, in above embodiment, for example, as hardware structures of processing units that execute various kinds of processing, such as the imaging controller 31, the registration unit 32, the notification unit 33, the image processing unit 34, the calibration unit 35, and the display controller 36, various processors shown below can be used. As described above, the various processors include a programmable logic device (PLD) as a processor of which the circuit configuration can be changed after manufacture, such as a field-programmable gate array (FPGA), a dedicated electrical circuit as a processor having a dedicated circuit configuration for executing specific processing such as an application-specific integrated circuit (ASIC), and the like, in addition to the CPU as a general-purpose processor that functions as various processing units by executing software (program).

One processing unit may be configured by one of the various processors, or may be configured by a combination of the same or different types of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, as represented by a system-onchip (SoC) or the like, there is a form of using a processor for realizing the function of the entire system including a plurality of processing units with one integrated circuit (IC) chip. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

The supplementary notes of the present disclosure will be described below.

Supplementary Note 1

An imaging control device that controls fluoroscopy of a subject in each of a plurality of fluoroscopy apparatuses that are used simultaneously in a case in which the fluoroscopy is performed in a plurality of directions, the imaging control device comprising at least one processor, in which the processor is configured to:

mutually register another fluoroscopy apparatus other than a fluoroscopy apparatus of which the imaging control device itself controls the fluoroscopy; and notify, in a case in which an instruction to start emitting radiation is given and the radiation is emitted from the fluoroscopy apparatus of which the imaging control device itself controls the fluoroscopy, the other fluoroscopy apparatus that the radiation has been emitted.

Supplementary Note 2

The imaging control device according to Supplementary Note 1, in which the processor is configured to:

set the fluoroscopy apparatus of which the imaging control device itself controls the fluoroscopy to a registration standby state;

search for the other fluoroscopy apparatus in a registration standby state; and mutually register the found other fluoroscopy apparatus.

Supplementary Note 3

The imaging control device according to Supplementary Note 1 or 2, in which the processor is configured to notify, in a case in which the instruction to start emitting the radiation is given, the other fluoroscopy apparatus that the emission of the radiation has started.

Supplementary Note 4

The imaging control device according to Supplementary Note 3, in which the instruction to start emitting the radiation is given by turning on a radiation irradiation switch of the fluoroscopy apparatus, and the processor is configured to notify the other fluoroscopy apparatus that the emission of the radiation has started by transmitting a radiation irradiation start flag to the other fluoroscopy apparatus.

Supplementary Note 5

The imaging control device according to any one of Supplementary Notes 1 to 4, in which the processor is configured to notify, in a case in which an instruction to stop emitting the radiation is given, the other fluoroscopy apparatus that the emission of the radiation has been stopped.

Supplementary Note 6

The imaging control device according to Supplementary Note 5, in which the instruction to stop emitting the radiation is given by turning off a radiation irradiation switch of the fluoroscopy apparatus, and the processor is configured to notify the other fluoroscopy apparatus that the emission of the radiation has been stopped by transmitting a radiation irradiation stop flag to the other fluoroscopy apparatus.

Supplementary Note 7

The imaging control device according to any one of Supplementary Notes 1 to 6, in which the fluoroscopy apparatus emits the radiation in a pulsed manner, and the processor is configured to notify the other fluoroscopy apparatus that the radiation has been emitted each time the radiation is emitted in a pulsed manner.

Supplementary Note 8

The imaging control device according to any one of Supplementary Notes 1 to 7, in which the processor is configured to perform, in a case in which a notification of the emission of the radiation from the other fluoroscopy apparatus is provided during the fluoroscopy of the subject, processing of reducing an influence of the radiation emitted from the other fluoroscopy apparatus on a fluoroscopic image acquired by the fluoroscopy.

Supplementary Note 9

The imaging control device according to Supplementary Note 8, in which the processing of reducing the influence of the radiation is scattered ray removal processing of removing a scattered ray component from the fluoroscopic image.

Supplementary Note 10

The imaging control device according to any one of Supplementary Notes 1 to 9, in which the processor is configured to perform, in a case of performing calibration of the fluoroscopy apparatus of which the imaging control device itself controls the fluoroscopy, the calibration at a timing at which a notification of the emission of the radiation from the other fluoroscopy apparatus is not provided.

Supplementary Note 11

The imaging control device according to any one of Supplementary Notes 1 to 10, in which the processor is configured to stop, in a case in which a notification of the emission of the radiation from the other fluoroscopy apparatus is provided during calibration of the fluoroscopy apparatus of which the imaging control device itself controls the fluoroscopy, the calibration.

Supplementary Note 12

An imaging control method in which a computer controls fluoroscopy of a subject in each of a plurality of fluoroscopy apparatuses that are used simultaneously in a case in which the fluoroscopy is performed in a plurality of directions, the imaging control method comprising:

mutually registering another fluoroscopy apparatus other than a fluoroscopy apparatus of which the imaging control device itself controls the fluoroscopy; and notifying, in a case in which an instruction to start emitting radiation is given and the radiation is emitted from the fluoroscopy apparatus of which the imaging control device itself controls the fluoroscopy, the other fluoroscopy apparatus that the radiation has been emitted.

Supplementary Note 13

An imaging control program causing a computer to execute processing of controlling fluoroscopy of a subject in each of a plurality of fluoroscopy apparatuses that are used simultaneously in a case in which the fluoroscopy is performed in a plurality of directions, the imaging control program comprising:

a step of mutually registering another fluoroscopy apparatus other than a fluoroscopy apparatus of which the imaging control device itself controls the fluoroscopy; and a step of notifying, in a case in which an instruction to start emitting radiation is given and the radiation is emitted from the fluoroscopy apparatus of which the imaging control device itself controls the fluoroscopy, the other fluoroscopy apparatus that the radiation has been emitted.

What is claimed is:

1. An imaging control device that controls fluoroscopy of a subject in each of a plurality of fluoroscopy apparatuses that are used simultaneously in a case in which the fluoroscopy is performed in a plurality of directions, the imaging control device comprising at least one processor, wherein the processor is configured to:

mutually register another fluoroscopy apparatus other than a fluoroscopy apparatus of which the imaging control device itself controls the fluoroscopy; and notify, in a case in which an instruction to start emitting radiation is given and the radiation is emitted from the fluoroscopy apparatus of which the imaging control device itself controls the fluoroscopy, the other fluoroscopy apparatus that the radiation has been emitted.

2. The imaging control device according to claim 1, wherein the processor is configured to:

set the fluoroscopy apparatus of which the imaging control device itself controls the fluoroscopy to a registration standby state;

search for the other fluoroscopy apparatus in a registration standby state; and mutually register the found other fluoroscopy apparatus.

3. The imaging control device according to claim 1, wherein the processor is configured to notify, in a case in which the instruction to start emitting the radiation is given, the other fluoroscopy apparatus that the emission of the radiation has started.

4. The imaging control device according to claim 3, wherein the instruction to start emitting the radiation is given by turning on a radiation irradiation switch of the fluoroscopy apparatus, and the processor is configured to notify the other fluoroscopy apparatus that the emission of the radiation has started by transmitting a radiation irradiation start flag to the other fluoroscopy apparatus.

5. The imaging control device according to claim 1, wherein the processor is configured to notify, in a case in which an instruction to stop emitting the radiation is given, the other fluoroscopy apparatus that the emission of the radiation has been stopped.

6. The imaging control device according to claim 5, wherein the instruction to stop emitting the radiation is given by turning off a radiation irradiation switch of the fluoroscopy apparatus, and the processor is configured to notify the other fluoroscopy apparatus that the emission of the radiation has been stopped by transmitting a radiation irradiation stop flag to the other fluoroscopy apparatus.

7. The imaging control device according to claim 1, wherein the fluoroscopy apparatus emits the radiation in a pulsed manner, and the processor is configured to notify the other fluoroscopy apparatus that the radiation has been emitted each time the radiation is emitted in a pulsed manner.

8. The imaging control device according to claim 1, wherein the processor is configured to perform, in a case in which a notification of the emission of the radiation from the other fluoroscopy apparatus is provided during the fluoroscopy of the subject, processing of reducing an influence of the radiation emitted from the other fluoroscopy apparatus on a fluoroscopic image acquired by the fluoroscopy.

9. The imaging control device according to claim 8, wherein the processing of reducing the influence of the radiation is scattered ray removal processing of removing a scattered ray component from the fluoroscopic image.

10. The imaging control device according to claim 1, wherein the processor is configured to perform, in a case of performing calibration of the fluoroscopy apparatus of which the imaging control device itself controls the fluoroscopy, the calibration at a timing at which a notification of the emission of the radiation from the other fluoroscopy apparatus is not provided.

11. The imaging control device according to claim 1, wherein the processor is configured to stop, in a case in which a notification of the emission of the radiation from the other fluoroscopy apparatus is provided during calibration of the fluoroscopy apparatus of which the imaging control device itself controls the fluoroscopy, the calibration.

12. An imaging control method in which a computer controls fluoroscopy of a subject in each of a plurality of fluoroscopy apparatuses that are used simultaneously in a case in which the fluoroscopy is performed in a plurality of directions, the imaging control method comprising:

mutually registering another fluoroscopy apparatus other than a fluoroscopy apparatus of which the imaging control device itself controls the fluoroscopy; and notifying, in a case in which an instruction to start emitting radiation is given and the radiation is emitted from the fluoroscopy apparatus of which the imaging control device itself controls the fluoroscopy, the other fluoroscopy apparatus that the radiation has been emitted.

13. A non-transitory computer-readable storage medium that stores an imaging control program causing a computer to execute processing of controlling fluoroscopy of a subject in each of a plurality of fluoroscopy apparatuses that are used simultaneously in a case in which the fluoroscopy is performed in a plurality of directions, the imaging control program comprising:

a step of mutually registering another fluoroscopy apparatus other than a fluoroscopy apparatus of which the imaging control device itself controls the fluoroscopy; and a step of notifying, in a case in which an instruction to start emitting radiation is given and the radiation is emitted from the fluoroscopy apparatus of which the imaging control device itself controls the fluoroscopy, the other fluoroscopy apparatus that the radiation has been emitted.

* * * * *